(12) United States Patent
Cole

(10) Patent No.: US 8,890,700 B2
(45) Date of Patent: Nov. 18, 2014

(54) EVALUATING SCATTERED-LIGHT SIGNALS IN AN OPTICAL HAZARD DETECTOR AND OUTPUTTING A DUST/STEAM WARNING OR A FIRE ALARM

(75) Inventor: Martin Terence Cole, Patterson Lakes (AU)

(73) Assignee: Siemens Aktiengesellschaft, Munich (DE)

( * ) Notice: Subject to any disclaimer, the term of this patent is extended or adjusted under 35 U.S.C. 154(b) by 95 days.

(21) Appl. No.: 13/816,331

(22) PCT Filed: Aug. 8, 2011

(86) PCT No.: PCT/EP2011/063591
§ 371 (c)(1),
(2), (4) Date: May 20, 2013

(87) PCT Pub. No.: WO2012/019987
PCT Pub. Date: Feb. 16, 2012

(65) Prior Publication Data
US 2013/0234856 A1 Sep. 12, 2013

(30) Foreign Application Priority Data

Aug. 11, 2010 (DE) .......................... 10 2010 039 230

(51) Int. Cl.
| | | |
|---|---|---|
| G08B 17/10 | (2006.01) | |
| G08B 17/107 | (2006.01) | |
| G01N 15/02 | (2006.01) | |
| G01N 21/53 | (2006.01) | |
| G01N 21/31 | (2006.01) | |

(52) U.S. Cl.
CPC .......... *G01N 21/3151* (2013.01); *G08B 17/107* (2013.01); *G01N 15/0205* (2013.01); *G01N 21/53* (2013.01)
USPC .......................................... 340/630; 340/627

(58) Field of Classification Search
USPC .......................................... 340/630, 627, 628
IPC .. G08B 17/107,17/103, 29/043; G01N 15/0205
See application file for complete search history.

(56) References Cited

U.S. PATENT DOCUMENTS 5,280,272 A * 1/1994 Nagashima et al. .......... 340/630
7,812,708 B2 10/2010 Müller et al.
(Continued)

FOREIGN PATENT DOCUMENTS

| CN | 1462418 | 12/2003 |
| CN | 101300612 | 11/2008 |

(Continued)

OTHER PUBLICATIONS

International Search Report for PCT/EP2011/063591, mailed on Mar. 22, 2012.

*Primary Examiner* — Shirley Lu
(74) *Attorney, Agent, or Firm* — Staas & Halsey LLP

(57) ABSTRACT

Particles to be detected are irradiated by first wavelength light and second wavelength light. The light that is scattered by the particles is converted into a first and second scattered-light signals. The two scattered-light signals are normalized with respect to one another such that the amplitude profile thereof approximately corresponds to larger particles such as dust and steam. Furthermore, an amplitude ratio is formed between the two scattered-light signals and an amplitude comparison value (90%) is set, which corresponds to a pre-determinable particle dimension in the cross-over region between smoke and dust/steam. Mainly the first scattered-light signal is evaluated if the amplitude ratio exceeds the amplitude comparison value (90%) and a dust/steam-density signal is emitted. In the other case, mainly the second scattered-light signal that is evaluated and a smoke-density signal is emitted.

16 Claims, 2 Drawing Sheets

(56) References Cited

U.S. PATENT DOCUMENTS 8,269,639 B2 9/2012 Cole
8,508,376 B2 8/2013 Knox et al.

FOREIGN PATENT DOCUMENTS

| CN | 101512613 | 8/2009 |
| CN | 101099186 | 1/2012 |
| DE | 102010039230.8 | 8/2010 |
| EP | 0 877 345 | 11/1998 |
| EP | 2112639 | 10/2009 |
| GB | 2319605 | 5/1998 |
| WO | 2005/043479 | 5/2005 |
| WO | 2008/064396 | 6/2008 |
| WO | PCT/EP2011/063591 | 8/2011 |

* cited by examiner

EVALUATING SCATTERED-LIGHT SIGNALS IN AN OPTICAL HAZARD DETECTOR AND OUTPUTTING A DUST/STEAM WARNING OR A FIRE ALARM

CROSS REFERENCE TO RELATED APPLICATIONS

This application is based on and hereby claims priority to International Application No. PCT/EP2011/063591 filed on Aug. 8, 2011 and German Application No. 10 2010 039230.8 filed on Aug. 11, 2010, the contents of which are hereby incorporated by reference.

BACKGROUND

The invention relates to method for evaluating two scattered-light signals of an optical hazard detector operating according to the scattered-light principle.

The invention further relates to an optical hazard detector with a detection unit operating in accordance with the scattered-light principle and with an associated electronic evaluation unit.

Furthermore it is generally known that particles with a size of more than 1 μm primarily involve dust, while particles with a size of less than 1 μm primarily involve smoke.

Such a method or such a hazard detector is known from international publication WO 2008/064396 A1. In the publication, for increasing the sensitivity for the detection of smoke particles, it is proposed that the second scattered-light signal be evaluated with blue light wavelength, if the amplitude ratio corresponds to a particle dimension of less than 1 μm. If on the other hand the amplitude ratio corresponds to a particle dimension of more than 1 μm, the difference is formed between the second scattered-light signal with blue light wavelength and the first scattered light with infrared wavelength. The differentiation inhibits the influence of dust and thus largely suppresses the triggering of a false alarm for the presence of a fire.

SUMMARY

Using this related art as its starting point, one possible object is to specify an expanded method of evaluating scattered-light signals as well as an improved optical hazard detector.

The inventor proposed a method for evaluating two scattered-light signals of an optical hazard detector operating according to the scattered-light principle. The particles to be detected are irradiated with light in a first wavelength range and with light in a second wavelength range. The light scattered by the particles is converted into a first and second scattered-light signal. The two scattered-light signals are normalized with respect to one another such that the amplitude profile thereof approximately corresponds for relatively large particles such as dust and steam. Furthermore an amplitude ratio is formed between the two scattered-light signals and an amplitude comparison value is defined which corresponds to a predeterminable particle dimension in the cross-over area from smoke to dust/steam. The two scattered-light signals are processed further in respect of fire characteristic variables depending on the current comparison result. For the proposed method, for the case in which the amplitude ratio exceeds the amplitude comparison value, it is at least mainly the first scattered-light signal that is evaluated and a dust/steam density signal is emitted and for the other case it is at least mainly the second scattered-light signal that is evaluated and a smoke density signal is emitted. "Mainly" means that as a maximum a weighting component of maximum 10% of the other respective scattered-light signal is evaluated. Preferably exclusively only the one scattered-light signal is evaluated in each case.

The idea at the core of proposals is that, as well as the emission of a smoke density signal for possible further processing, an additional dust/steam density signal is also emitted for possible further processing. This signal can for example provide information about whether an impermissibly high dust density and/or (water) steam density is present. A dust density which is too high can represent a high safety risk and for example accelerate the spread of a fire or promote deflagrations or explosions. At the same time a steam density or water steam density which is too high can be an indication of a hot water leak such as in a heating system for example. The additional dust/steam density signal can advantageously deliver further information, especially in combination with the steam density signal, as regards an area to be monitored.

According to a first method variant the particles are irradiated with infrared light of a wavelength of 600 to 1000 nm, especially with a wavelength of 940 nm±20 nm, and with blue light of the wavelength of 450 to 500 nm, especially with a wavelength of 470 nm±20 nm. The light can originate from a single light source for example which sends out infrared light and blue light alternating over time. It can also originate from two separate light sources, especially from a blue light-emitting diode and from an infrared light-emitting diode. Especially advantageous in this case is the use of an IR light-emitting diode with a wavelength at 940 nm±20 nm as well is the blue light-emitting diode with a wavelength of 470 nm±20 nm.

Preferably the predeterminable particle dimension has a value ranging from 0.5 to 1.1 especially a value of around 1 μm. According to a further method variant the amplitude comparison value is set to a value ranging from 0.8 to 0.95, especially to a value of 0.9, or to its reciprocal value. A value of 0.9 in such cases corresponds to a particle dimension of 1 μm.

According to a further method variant the dust/steam density signal is compared with a first signal limit. If the limit is exceeded the dust/stem density signal is then emitted as a dust/steam warning. Furthermore the smoke density signal is compared with a second signal limit and this smoke density signal is emitted as a fire alarm when the limit is exceeded. Thus no message is emitted in normal operation without any further incidents. By contrast, depending on the amplitude ratio for a particle density that is too high, either a dust/steam warning or a fire alarm is output. The respective alarm can be emitted using an optical or acoustic transducer. As an alternative or in addition it can be output by wire and/or wirelessly to a fire alarm control center.

The inventor further proposed an optical hazard detector with a detection unit operating in accordance with the scattered-light principle and with an associated electronic evaluation unit. The detection unit has at least one illumination device to irradiate particles to be detected and at least one optical receiver for detection of light scattered by the particles. The light emitted by the at least one illumination device lies in at least one first wavelength range and in a second wavelength range. The at least one optical receiver is sensitive to the first and/or second wavelength range as well as being embodied for converting the received scattered light into a first and second scattered-light signal. The evaluation unit has a first unit for normalizing the two scattered-light signals such that their amplitude profile largely corresponds for larger particles such as dust and steam. It has a second unit for forming an amplitude ratio between the two scattered-light signals. Finally, it has a third unit for comparing an amplitude comparison value, which corresponds to a predeterminable particle dimension in the cross-over region between smoke and dust/steam, with the currently formed amplitude ratio. The third unit is also configured for further processing of the two scattered-light signals for fire characteristic variables, depending on the current comparison result. The electronic evaluation unit of the detector has a fourth unit which is configured to at least mainly evaluate the first scattered-light signal and to emit a dust/steam density signal in the event of the amplitude ratio exceeding the amplitude comparison value and which are configured for the other case to at least mainly evaluate the second scattered-light signal and to emit a smoke density signal.

The electronic evaluation unit can be an analog and/or digital electronic circuit featuring for example A/D converters, amplifiers, comparators, operational amplifiers for normalizing the scattered-light signals, etc. In the simplest case this evaluation unit is a microcontroller, i.e. a processor-assisted electronic processing unit, which is usually present "in any event" for overall control of the hazard detector. The evaluation unit is preferably emulated by program steps which are executed by the microcontroller, if necessary by including electronically-stored table variables, e.g. for the comparison variables and signal limits. A corresponding computer program can be stored in a non-volatile memory of the microcontroller. Alternatively it can be loaded from an external memory. Furthermore the microcontroller can have one or more integrated ND converters for measuring and recording the two scattered-light signals. It can for example also feature D/A converters, via which the radiation intensity of at least one of the two light sources can be set for normalizing the two scattered-light signals.

According to an embodiment of the optical hazard detector, its electronic evaluation unit has a fifth unit for comparing the dust/steam density signal with a first signal limit and for comparing the smoke density signal with a second signal limit. Further the fifth unit has a signaling device for signaling a dust/steam warning and a fire alarm if the respective signal limit is exceeded.

Preferably the hazard detector is a fire alarm and especially an aspirating smoke alarm and with a pipe system able to be connected thereto for monitoring the air sucked in from rooms and facilities requiring monitoring.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
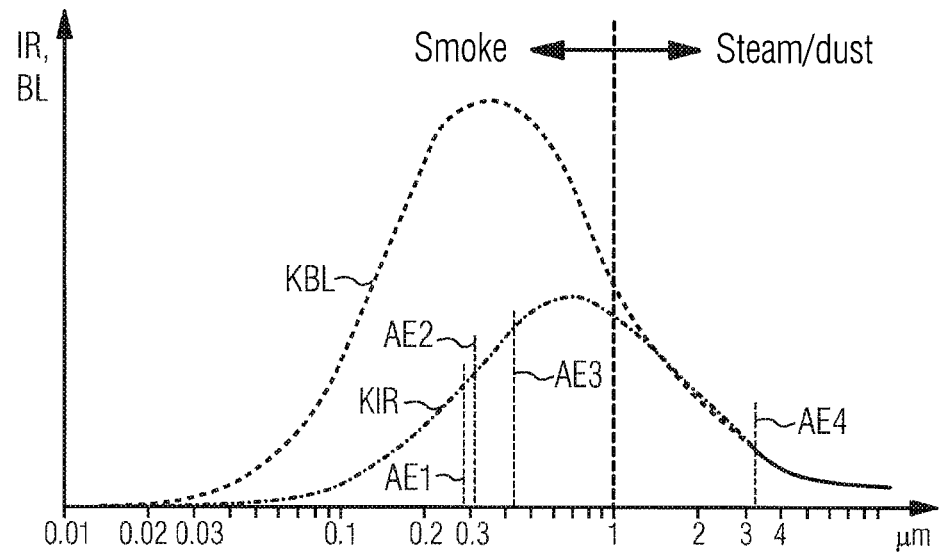
FIG. 1 shows the relative signal level of a respective amplitude profile of for example infrared and blue scattered light, plotted logarithmically in μm and with the average particle dimension of typical smoke and dust particles indicated.

Reference will now be made in detail to the preferred embodiments of the present invention, examples of which are illustrated in the accompanying drawings, wherein like reference numerals refer to like elements throughout.

FIG. 1 shows the respective relative signal level IR, BL of an amplitude profile KIR, KBL, of for example infrared and blue scattered light, plotted in μm and with an average particle dimension indicated for smoke and steam particles AE1-AE4 (aerosols) for example.

AE1 plots an entry for the average smoke particle dimension for burning wool at approximately 0.28 μm, AE2 the smoke particle dimension for a burning wick at approximately 0.31 μm, AE3 the smoke particle dimension for burnt toast at approximately 0.42 μm and AE3 the average dust particle dimension for Portland cement at approximately 3.2 μm. Also entered is a dashed line at 1 μm, which represents an empirical boundary between smoke and dust/steam for typical particles to be expected. Depending on the environment to be monitored—it can also be defined to range from 0.5 to 1.1 μm.

KIR indicates the amplitude profile of the infrared scattered-light signal IR with a wavelength of 940 nm and KBL indicates the amplitude profile of the blue scattered-light signal BL with a wavelength of 470 nm. In the diagram shown, the two scattered-light signals IR, BL are already normalized in relation to each other such that their amplitude profile approximately correspond for larger particles such as dust and steam. In the present example the amplitude profile approximately corresponds for a particle dimension of more than 3 μm.

As FIG. 1 shows, the blue light is scattered more at smaller particles and the infrared light more at larger particles.

Figure 2:
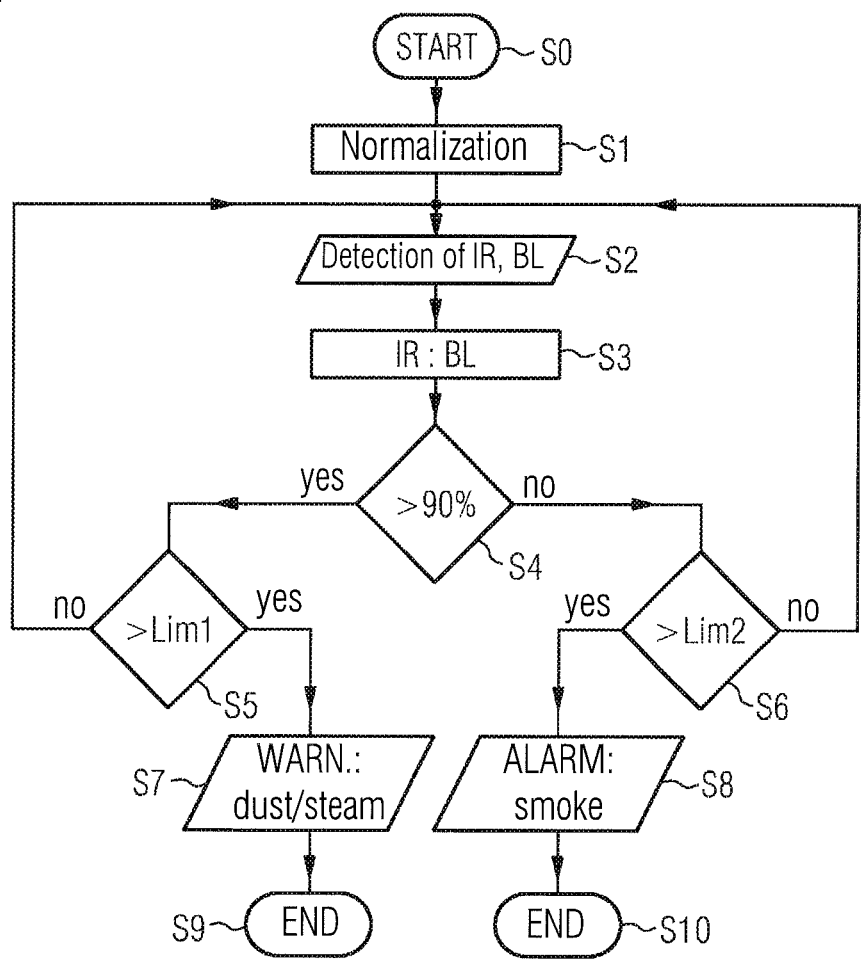
FIG. 2 shows a typical flow diagram in accordance with a method variant to illustrate the proposed method.

FIG. 2 shows a typical flow diagram already according to a method variant for explaining the proposed method. The individual steps S1-S10 can be emulated by suitable program steps of a computer program and executed on a processor-assisted processing unit of a hazard detector, such as on a microcontroller for example.

S0 designates a start step. In this initialization step for example an amplitude comparison value can be defined which corresponds to a predeterminable particle dimension in the cross-over area from smoke to dust/steam, such as at 1 μm for example. In this step S0 signal limits Lim1, Lim2 can also already be defined, in order to generate or emit a dust/steam warning WARN from an output dust/steam density signal or a fire alarm ALARM from an emitted smoke density signal.

In step S1 the two scattered-light signals IR, BL are normalized in relation to one another such that their amplitude profile approximately corresponds for larger particles such as dust and steam. This calibration process is preferably repeated during commissioning of a hazard detector and if necessary cyclically thereafter.

In typical normal operation of the hazard detector in step S2 the light scattered from the particles is converted into the first and second scattered-light signal IR', BL' and is thus detected.

In step S3 an amplitude ratio between the two scattered-light signals IR, BL is formed. In the present case for example the ratio IR:BL is formed. As an alternative the reciprocal value of the two scattered-light signals IR, BL can also be formed.

In step S4 the current amplitude ratio is compared with the pre-determined amplitude comparison value of for example 90% or with its reciprocal value in the event of reciprocal amplitude ratio formation.

In accordance with the method variants already present, in a step S5, for a positive comparison result the emitted dust/steam density signal is compared again with the first signal limit Lim1. Finally, if the limit is exceeded, the dust/steam warning WARN is emitted. Otherwise the method branches back to step S2.

Furthermore in accordance with the present method variants, in a step S6, for a negative comparison result the emitted smoke density signal is compared again with the second signal limit Lim2 and if this limit is exceeded the fire alarm ALARM is emitted. Otherwise the method branches back to step S2.

S9 and S10 respectively designate the end step.

Figure 3:
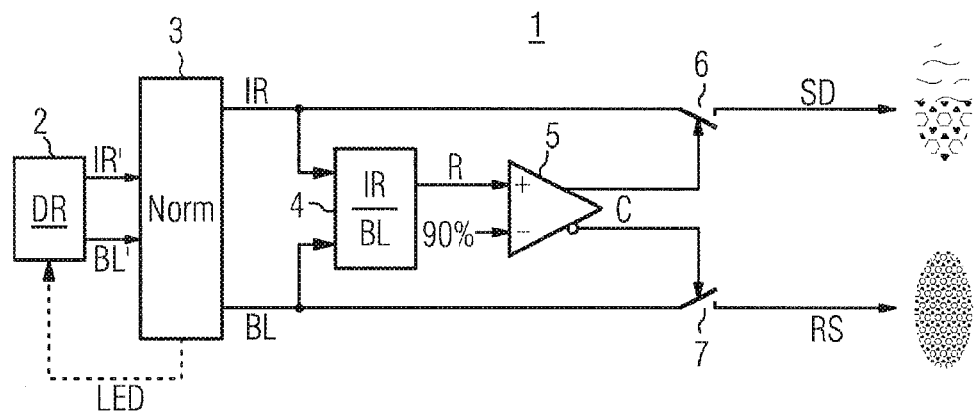
FIG. 3 shows an example of an proposed hazard detector according to a first embodiment and FIG. 4 shows an example of a hazard detector according to a second embodiment.

FIG. 3 shows an example of the proposed hazard detector 1 according to a first embodiment.

The optical hazard detector 1 is especially a fire alarm or a smoke alarm. It can be embodied as a point detector. It can also be embodied with a connectable pipe system for monitoring the air sucked in from rooms and facilities to be monitored. Furthermore the hazard detector has a detection unit 2 operating according to the scattered-light principle. The latter can be disposed for example in a closed measurement chamber with a detection space DR located therein. In this case the fire or smoke alarm 1 is a closed fire or smoke alarm. As an alternative or in addition the fire or smoke alarm 1 can be a so-called open fire or smoke alarm, having a detection space DR disposed outside the detection unit 2.

The detection unit 2 has at least one illumination device not shown in any greater detail for irradiation of particles to be detected in the detection space DR as well as at least one optical receiver for detection of the light scattered from the particles. Preferably the detection unit has an infrared light-emitting diode with a wavelength in the first wavelength range of 600 to 1000 nm, especially with a wavelength of 940 nm±20 nm, and a blue light-emitting diode with a wavelength in the second wavelength range of 450 to 500 nm, especially with a wavelength of 470 nm±20 nm for illumination. Furthermore the detection unit 2 has at least one optical receiver which is sensitive to the first and/or second wavelength range and which is embodied to convert the received scattered light into a first and a second (unnormalized) scattered-light signal IR', BL'. Preferably such an optical receiver is a photodiode or a phototransistor. The two scattered-light signals IR', BL' can also be formed offset in time by a single optical receiver sensitive for both wavelength ranges. In this case the particles are irradiated alternately, preferably with the blue light and infrared light and synchronized thereto the first and second scattered-light signal IR', BL' is formed.

Furthermore the hazard detector 1 has an evaluation unit connected by a number of data or signal transmitters to the detection unit 2. The first unit 3 is designed for normalization of the two (unnormalized) scattered-light signals IR', BL' in respect of one another, so that their amplitude profile roughly corresponds for larger particles such as dust and steam. This first unit 3 can feature adjustable amplifiers or attenuation elements for example, in order to normalize the signal levels of the two scattered-light signals IR', BL' in respect of one another. It can also provide one or two output signals LED, in order to set the respective light intensity of the illumination device in the detection unit 2 so that the amplitude profile of the two scattered-light signals IR', BL' again roughly corresponds for larger particles such as dust and steam. IR, BL ultimately designate the two normalized scattered-light signals.

The evaluation unit also has a second unit 4 for forming an amplitude ratio R between the two scattered-light signals IR, BL. In the present example this unit 4 is an analog divider.

Furthermore the evaluation unit has a third unit 5 in the form of a comparator. The third unit 5 is embodied for comparing an amplitude comparison value of 90%, which corresponds to a predeterminable particle dimension in the cross-over area from smoke to dust/steam, with the amplitude ratio R currently formed. Based on this current comparison result C the two scattered-light signals IR, BL are then further processed for fire characteristic variables.

The further processing is undertaken by fourth units 6, 7 of the evaluation unit. The unit 6 is configured to at least mainly evaluate the first scattered-light signal IR and to emit a dust/steam density signal SD in the event of the amplitude ratio R exceeding the amplitude comparison value of 90%. It is also configured for the other case of at least mainly evaluating the second scattered-light signal BL and emitting a smoke density signal RS.

In the present case an especially easily implemented further processing of the two scattered-light signals IR, BL is shown, in that two controllable switches 6, 7 are controlled as a function of the comparison result C in order to either through connect the first scattered-light signal IR as a dust/steam density signal SD or to respectively through connect or suppress the second scattered-light signal BL as a smoke density signal RS.

Figure 4:
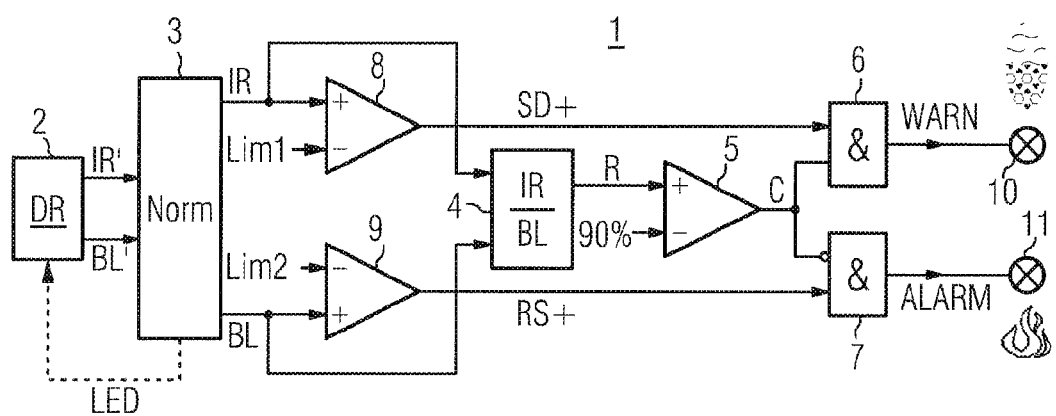

FIG. 4 shows an example of a hazard detector 1 according to a second embodiment. This embodiment differs from the previous in that the two scattered-light signals IR, BL are still each compared with a predeterminable signal limit Lim1, Lim2. In the present example this is done by two comparators 8, 9. On the output side the two comparators 8, 9 provide a corresponding control signal SD+, RS+, which is through connected as a function of the comparison result C as a dust/steam warning WARN or as a fire alarm ALARM. In addition in the present example the warning or the alarm is signaled by activating an optical alarm indicator in the form of two lamps 10, 11.

Preferably all components of the evaluation unit shown in FIG. 3 and FIG. 4 are implemented by a processor-assisted processing unit, such as by a microcontroller for example. The latter preferably features integrated A/D converters for detecting the two scattered-light signals IR', BL' and also D/A converters and/or digital output ports for the output of the smoke density signal RS, of the dust/steam density signal SD and also the fire alarm ALARM and the dust/steam warning WARN. The evaluation unit is preferably emulated by suitable program operations, which are then executed on the microcontroller.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide* v. *DIRECTV*, 69 USPQ2d 1865 (Fed. Cir. 2004).

The invention claimed is:

1. A method for hazard detection using a scattered-light principle, comprising:
   irradiating particles to be detected with first light in a first wavelength range and second light in a second wavelength range;
   scattering the first and second lights by the particles to produce first and second scattered-light signals respectively from the first and second lights;
   normalizing the first and second scattered-light signals with respect to one another to produce first and second normalized scattered-light signals having amplitude profiles approximately corresponding to steam or dust particles;

forming an amplitude ratio between the normalized scattered-light signals;

defining an amplitude comparison value, which corresponds to a particle dimension in a cross-over area from smoke to dust/steam;

comparing the amplitude ratio with the amplitude comparison value, for processing the normalized scattered-light signals for fire characteristic values;

if the amplitude ratio exceeds the amplitude comparison value, evaluating the first normalized scattered-light signal and emitting a dust/steam density signal; and if the amplitude ratio is less than or equal to the amplitude comparison value, evaluating the second normalized scattered-light signal and emitting a smoke density signal.

2. The method as claimed in claim 1, wherein
the first light is infrared light having a wavelength of from 600 to 1000 nm, and
the second light is blue light having a wavelength of from 450 to 500 nm.

3. The method as claimed in claim 1, wherein
the first light is infrared light having a wavelength of 940 nm±20 nm, and
the second light is blue light having a wavelength of 470 nm±20 nm.

4. The method as claimed in claim 1, wherein the particle dimension in the cross-over area from smoke to dust/steam has a value ranging from 0.5 to 1.1 μm.

5. The method as claimed in claim 1, wherein the particle dimension in the cross-over area from smoke to dust/steam has a value of approximately 1 μm.

6. The method as claimed in claim 1, wherein the amplitude comparison value has a value ranging from 0.8 to 0.95 or a reciprocal value thereof.

7. The method as claimed in claim 1, wherein the amplitude comparison value has a value of approximately 0.9 or a reciprocal value thereof.

8. The method as claimed in claim 1, wherein
the dust/steam density signal is compared with a first signal limit and, if the dust/steam density signal exceeds the first signal limit, the dust/steam density signal is emitted as a dust/steam warning, and
the smoke density signal is compared with a second signal limit and, if the smoke density signal exceeds the second signal limit, the smoke density signal is emitted as a fire alarm.

9. An optical hazard detector comprising:
a detection device comprising:
at least one light source to irradiate particles to be detected with first light in a first wavelength range and second light in a second wavelength range; and
an optical receiver to detect first and second scattered-light signals produced by the particles respectively scattering the first and second lights, the optical receiver being sensitive to the first wavelength range and/or the second wavelength range; and
the electronic evaluation unit comprising:
a first unit to normalize the first and second scattered-light signals and produce first and second normalized scattered-light signals having amplitude profiles that approximately correspond to dust or steam;
a second unit to form an amplitude ratio between the normalized scattered-light signals;
a third unit to compare the amplitude ratio with an amplitude comparison value, which corresponds to a particle dimension in a cross-over area from smoke to dust/steam;
a fourth unit to evaluate the first normalized scattered-light signal and emit a dust/steam density signal if the amplitude ratio exceeded the amplitude comparison value, and to evaluate the second normalized scattered-light signal and emit a smoke density signal if the amplitude ratio was less than or equal to the amplitude comparison value.

10. The optical hazard detector as claimed in claim 9, wherein the at least one light source in the detection device comprises:
an infrared light-emitting diode to produce the first light, the first wavelength range being 600 to 1000 nm; and
a blue light-emitting diode to produce the second light, the second wavelength range being 450 to 500 nm.

11. The optical hazard detector as claimed in claim 9, wherein the at least one light source in the detection device comprises:
an infrared light-emitting diode to produce the first light, the first wavelength range being 940 nm±20 nm; and
a blue light-emitting diode to produce the second light, the second wavelength range being 470 nm±20 nm.

12. The optical hazard detector as claimed in claim 9, wherein the particle dimension in the cross-over area from smoke to dust/steam has a value ranging from 0.5 to 1.1 μm.

13. The optical hazard detector as claimed in claim 9, wherein the particle dimension in the cross-over area from smoke to dust/steam has a value of approximately 1 μm.

14. The optical hazard detector as claimed in claim 9, wherein the amplitude comparison value has a value ranging from 0.8 to 0.95 or a reciprocal value thereof.

15. The optical hazard detector as claimed in claim 9, wherein the amplitude comparison value has a value of approximately 0.9 or a reciprocal value thereof.

16. The optical hazard detector as claimed in claim 9, wherein the electronic evaluation unit has a fifth unit to:
compare the dust/steam density signal with a first signal limit and produce a dust/steam warning if the dust/steam density signal exceeds the first signal limit; and
compare the smoke density signal with a second signal limit and produce a fire alarm if the smoke density signal exceeds the second limit value.

* * * * *